United States Patent

Jagner et al.

[11] Patent Number: 5,891,322
[45] Date of Patent: Apr. 6, 1999

[54] ELECTROANALYSIS PROCESS USING POTENTIOMETRY WITH COULOMETRIC STRIPPING (ELUTION)

[75] Inventors: Daniel Jagner, Partille, Sweden; Gilles Moninot, Villeurbanne, France

[73] Assignee: Radiometer Analytical SA, Villeurbanne, France

[21] Appl. No.: 735,306

[22] Filed: Oct. 22, 1996

[30] Foreign Application Priority Data

Oct. 27, 1995 [FR] France ................................. 95 12960

[51] Int. Cl.⁶ ....................................................... G01N 27/26
[52] U.S. Cl. ........................ 205/789; 204/405; 204/434; 205/775; 205/788.5; 205/789.5
[58] Field of Search ................................... 204/434, 405; 205/775, 789, 789.5, 788.5

[56] References Cited

U.S. PATENT DOCUMENTS 5,391,270  2/1995  Gui ........................................... 204/434

OTHER PUBLICATIONS

Electroanalysis, vol. 4, No. 3, Mar. 1992, pp. 267–273, D. Jagner, "A Novel Batch Electrode Design for use in Stripping Potentiometry Facilititing Medium Exchange".
International Publication No. WO 93/16378, published Aug. 19, 1996.
Electroanalysis, vol. 7, No. 7 Jul. 1995, pp. 614–618, D. Jagner, "Coulometric Stripping Potentiometry".
Electroanalysis, vol. 5, No. 4, May 1993, pp. 283–288, D. Jagner, "Simplified Stripping Potentiometry Methodology: Application to the Determination of Lead in Wine".
Analytica Chima Acta, vol. 267, No. 1, 11 Sep. 1992, pp. 165–169, D. Jagner, "Stripping Potentiometry for Organolead Compounds: Application to the Determination of Total Lead in Gasoline".

*Primary Examiner*—T. Tung
*Attorney, Agent, or Firm*—Nikaido Marmelstein Murray & Oram, LLP

[57] ABSTRACT

Electroanalysis of an electroactive, and especially ionized, species, in trace form, in a liquid sample, is by potentiometry with coulometric stripping (elution), and is by employing a working electrode in electrical contact with the sample. A practically exhaustive electrolysis, or a practically exhaustive complexing with adsorption, of the electroactive species, a main coulometric stripping and at least two poststripping cycles including a post-electrolysis step and a poststripping step are performed in succession. By a particular choice of the operating parameters and of the measured parameters it is possible to determine automatically the equivalent mean chemical current, for example for oxidation, competing with the current applied to the working electrode, during the stripping stage. This is done directly from the liquid sample which is being analyzed. As a result, the required concentration of the species is determined without previous calibration.

13 Claims, 4 Drawing Sheets

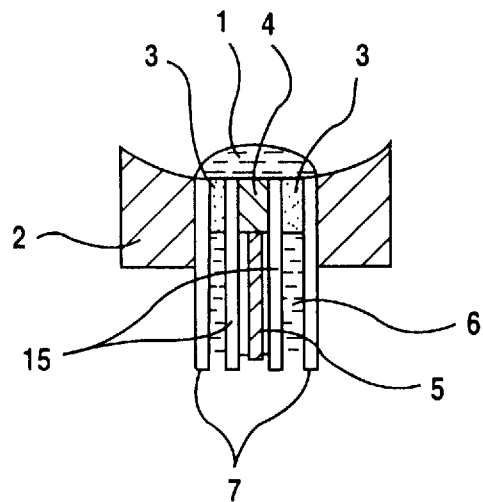
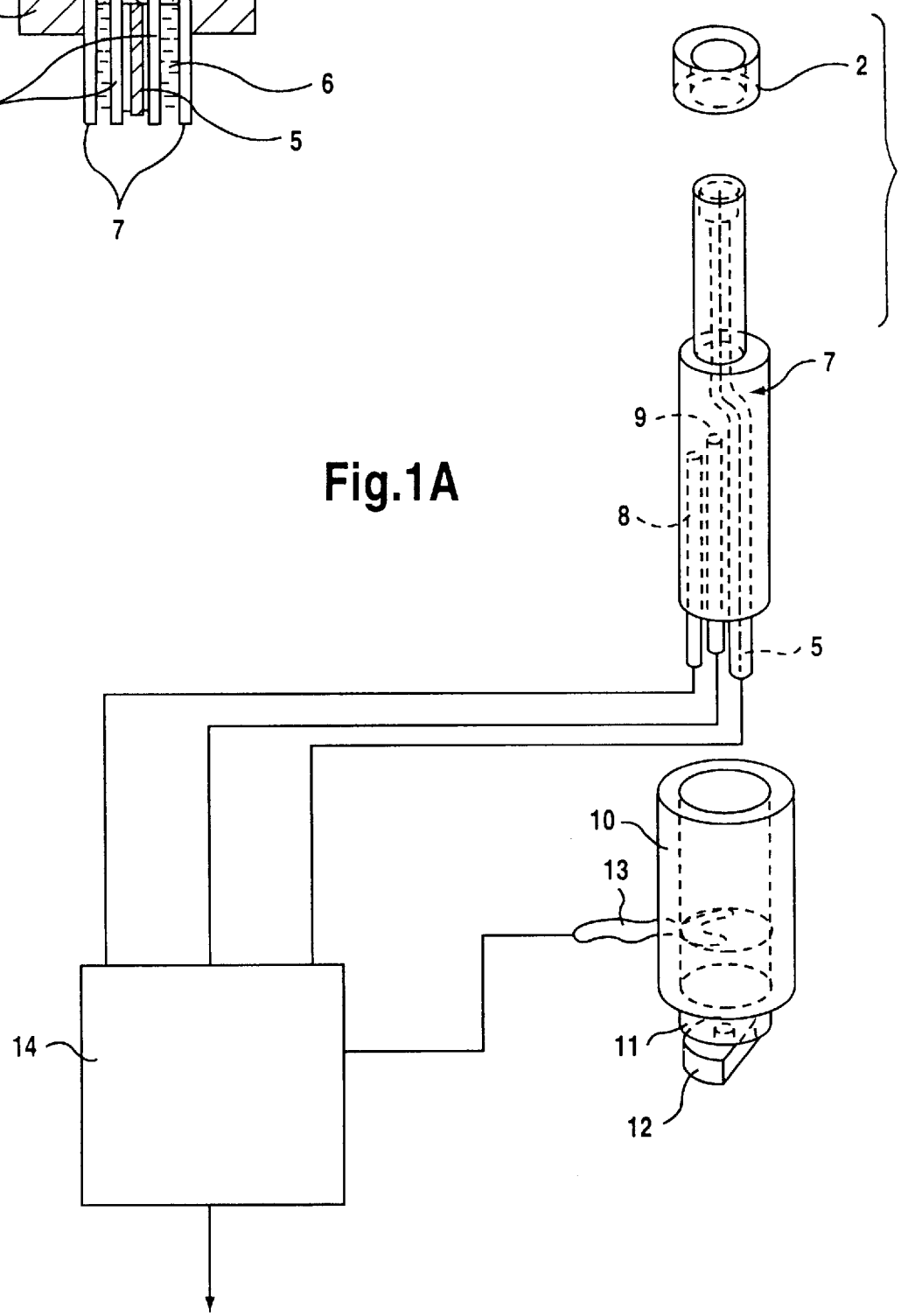
Fig.1B
Fig.1A

ELECTROANALYSIS PROCESS USING POTENTIOMETRY WITH COULOMETRIC STRIPPING (ELUTION)

The present invention relates to the electroanalysis of at least one electroactive, and especially ionized, species in an initial oxidation state (Eo), hereinafter called A, in trace form, in a liquid sample, which hereinafter has the volume V, by potentiometry with coulometric stripping (elution), this being done while employing a working electrode in electrical contact with this sample.

BACKGROUND OF THE INVENTION

In accordance with the present invention an "electroactive species" is intended to mean a chemical species, in the broadest sense, capable of undergoing changes in the oxidation state. This chemical species may be, for example, an atom, an ion, a molecule, a complex or a molecular system comprising ligands. In accordance with the invention and as described below, this species must be capable of being retained in one of its oxidation states on or in the working electrode by any suitable physical, chemical or physico-chemical mechanism, for example by adsorption, amalgamation or the like.

A "liquid sample" is intended to mean any quantity of a liquid medium in which the electroactive, and especially ionized, species is present in trace form, regardless of whether the liquid medium to be analyzed is placed directly in contact with the working electrode or is diluted or mixed beforehand with a liquid matrix, especially a complexing solvent, and/or with an agent modifying the oxidation state of the electroactive species. Prior to the electroanalysis the liquid medium may or may not be divided up, so as to subject to the electroanalysis optionally a determined fraction of said medium.

"In trace form" is intended to mean molar concentrations per unit volume in the original liquid medium which are at most equal to 10 $\mu$mol/l and preferably included according to the invention between 0.01 and 10 $\mu$mol/l, or weight concentrations at most equal to 1 mg/l and included between 1 and 1000 $\mu$g/l.

As stated already, the electroactive species must be capable of changing the oxidation state when a current or a potential is applied, preferably on electrical contact with a working electrode, while being deposited and being retained on the latter, by any suitable physical and/or chemical means such as the formation of an amalgam, dissolving in, or depositing on, a metal phase, for example gold, complexing, adsorption, absorption or else using electrostatic forces of attraction.

The electroactive species under consideration may be equally well cations, noble metals, anions, molecules or else complexes. Examples which will be mentioned are especially lead, cadmium, copper, bismuth, thallium, nickel, zinc, silver, platinum and halides as electroactive species capable of being detected and quantified according to the present invention.

Also, in accordance with the invention and as will be seen later, the electroactive species considered is capable of changing in oxidation state during the coulometric stripping, that is to say of being oxidized or reduced by means of a third element dissolved in the sample.

In order to make use of an electroanalysis according to the invention the electroactive species must pass through a number of oxidation states different from one another or some of them being the same ones, but the total number of electrons transferred during each stripping of the analysis must be known. These states are the following:

a zero or initial state (Eo) existing after preparation of the sample;

a first state (EI), equal to or different from the initial state (Eo), existing after a main electrolysis or adsorption stage;

a second state (EII), different from the first state (EI), different from or equal to the state (Eo), existing after a main coulometric stripping step;

and a third state (EIII) different from the second state (EII), different from or equal to the state (EI) and existing after at least one post-electrolysis step followed by a coulometric poststripping.

By way of preferred example of application of an electroanalysis according to the invention, but without any exclusiveness being implied, reference will be made to the investigation and to the quantification of heavy metals, in trace form, directly in a sample of whole blood, in the presence of dissolved and interfering oxygen.

DESCRIPTION OF THE PRIOR ART

The electroanalytical technique of potentiometry with coulometric stripping has been extensively described and defined in the available scientific and technical literature. Reference will be made in particular to the thesis published by Mr Yudong Wang, entitled "Stripping Potentiometry: Novel Methodology and Electrode Design", of the Department of Analytical and Marine Chemistry, University of Göteborg and Chalmers University of Technology, Göteborg, 1994. An overriding advantage of this technique is that it does not require previous calibration, for example with standard liquid samples, since in theory it suffices to measure an oxidation or reduction time, with a constant current, in order to determine the quantity and the concentration of the species, the stripping being finished when a predetermined stoppage potential is observed or detected between the working and reference electrodes. Another advantage of this technique is that it is independent, where the measurement performed is concerned, of the area of the working electrode in contact with the liquid sample.

Conventionally, and in its elementary form, potentiometry with coulometric elution, or coulometric stripping, consists in performing the following stages, as illustrated diagrammatically by FIGS. 3 and 4. In these figures the numerical references 16, 17 and 18 denote a working electrode, a drop of sample to be analyzed and a film of mercury respectively:

(a) during a main stage there is performed either a practically exhaustive electrolysis of the electroactive species, which is present in an initial state (Eo), at a predetermined potential, or a practically exhaustive complexing of said species with adsorption onto said electrode, while creating a convection regime in the vicinity of the liquid sample/working electrode interface, whereby practically all the electroactive species is deposited and retained, in a first oxidation state (EI), equal to or different from the initial state (EO), on the working electrode; if appropriate, the electrolysis and said convection regime are stopped; FIG. 3 thus shows the formation of a mercury amalgam in the form of film 18 and of electroactive species from a drop 17 deposited onto the electrode 16, after application of an electrolysis potential and of convection;

(b) during a main coulometric stripping stage, represented by FIG. 4, a predetermined current is applied to the working electrode 16, and this causes a change in the oxidation state of the species (A), from the state (EI) to a second state (EII); this has the effect of detaching and diffusing practically all the electroactive species, in oxidized or reduced form from the working electrode 16 into the sample 17; the value of the predetermined oxidation or reduction current, in relation with the measured time of the coulometric stripping stage, makes it theoretically possible to determine the quantity, and hence the concentration, of the electroactive species originally present in the liquid sample 17.

This basic technique has been developed and improved in various forms. In particular, in accordance with the paper entitled "Coulometric Stripping Potentiometry", by Daniel Jagner and Yudong Wang, forming part of the thesis identified above, it is known to repeat the stripping or elution several times, according to a technique known as "multi-stripping", by repeating a number of times the following coulometric poststripping cycle, as illustrated by FIGS. 5 and 6, in which the references are the same as in FIGS. 3 and 4:

(c.a) during a post-electrolysis step a predetermined potential is applied to the working electrode 16 for a time which is shorter than that of the main stage (a), in this case, of electrolysis, account being taken of the ceasing of the convection regime existing during stage (a); this predetermined potential makes it possible to change the second oxidation state (EII) of the species (A) to a third state (EIII), in the case of at least one portion of said species which has diffused into the liquid sample 17 during the stripping stage (b), but which has not had the time to diffuse too far from the working electrode 16 (cf. FIG. 5);

(c.b) during a poststripping step a predetermined current, strictly equal to the predetermined current of the main coulometric stripping stage (b) is applied to the working electrode 16, causing a change in the oxidation state of the species (A) from the state (EII) to the state (EIII), in order to detach and diffuse the electroactive species from the working electrode 16 into the liquid sample 17 (cf. FIG. 6).

By employing the potentiometric and coulometric technique defined above it is possible, in theory, to determine the concentration of the electroactive species (A) solely from the predetermined oxidation or reduction current during the stripping stage, and from the measurement of the duration of the latter. In practice, account must be taken of the third elements, oxidizing or reducing, which are present in the liquid medium, generating by way of interference so to speak an oxidation or reduction equivalent mean current, called $i_{chem}$, during the coulometric stripping stage.

Thus, and by way of example, when considering the electroanalysis of a heavy metal in a liquid sample, with a working electrode containing a mercury film or drop, interfering oxidizing agents, for example oxygen dissolved in the water, must exist in the liquid medium in a substantially constant concentration if the atmosphere above the oxidation cell is the surrounding air. This problem can be avoided by maintaining an inert atmosphere around the analysis cell, for example by purging the analysis system with nitrogen. However, such an action is burdensome and costly to implement, in terms of means and time, and this prevents its application for the purpose of routine analyses.

For each electroactive species the determination and the taking of this oxidation or reduction equivalent mean current into account determine the accuracy of the measurement of the concentration or quantity of the electroactive species.

Until now, and as taught by the abovementioned publication, the oxidation or reduction equivalent mean current, $i_{chem}$ was obtained for each electroactive species by a series of separate measurements, preliminary to the actual analysis, by starting with a liquid sample which had a predetermined concentration of electroactive species and by varying the stripping current for each measurement. In this way the oxidation or reduction equivalent mean current, $i_{chem}$, can be obtained by plotting a curve which has the reciprocal of the stripping time as ordinate and the stripping current as abscissa, and by performing a linear regression starting with this curve and an extrapolation for a stripping current equal to 0.

Of course, the need to carry out this series of preliminary measurements decreases the attractiveness of potentiometry with coulometric stripping as a method of electroanalysis. An objective of the present invention is therefore to overcome this disadvantage by providing an electroanalysis process and device making it possible to obtain the value of the oxidation or reduction equivalent mean current, $i_{chem}$, from the liquid sample alone and during the actual measurement of the concentration or quantity of the electroactive species.

SUMMARY OF THE INVENTION

In accordance with the invention the above-mentioned objective is met by starting with the following choices, in combination:

first of all essentially the multi-stripping described and defined above is used for the electroanalysis;

the following operating conditions are then fixed:

(i) the coulometric poststripping current during the previously defined stage (c.b) of a poststripping cycle is fixed equal to the coulometric stripping current of the first stripping cycle (b), namely $i_{ox1}$, and the coulometric poststripping current of another poststripping cycle, namely $i_{ox2}$ is different from, and especially smaller than $i_{ox1}$;

(ii) the coulometric poststripping current, $i_{ox2}$, during the previously defined step (c.b) of a poststripping cycle is different from, and especially smaller than, the main stripping current $i_{ox1}$, and the coulometric poststripping current $i_{ox2}$ of another poststripping cycle is strictly equal to $i_{ox2}$.

By measuring the main coulometric stripping time $t_{s1}$, and the coulometric poststripping times $t_{s2}$ and $t_{s3}$, respectively, of the two successive coulometric poststripping cycles, the oxidation or reduction equivalent mean current at the working electrode, $i_{chem}$, is determined from the measured sample alone, according to the equation (Ia), (Ib) or (Ic):

$$i_{chem} = (t_{s3} \cdot i_{ox2} - f \cdot t_{s2} \cdot i_{ox1})/(f \cdot t_{s2} - t_{s3}) \tag{Ia}$$

in which f is equal to $(t_{s2}/t_{s1}) \cdot (n_{1-2}/n_{3-2})$ or $$i_{chem} = (\alpha i_{ox1} - i_{ox2})/(1-\alpha) \tag{Ib}$$

in which $\alpha = [(t_{s1} \cdot t_{s3}/t_{s2}^2) \cdot (n_{3-2}/n_{1-2})]^{1/2}$ or $$i_{chem} = \frac{[n_{1-2} \cdot t_{s2} \cdot i_{ox2}) - (n_{3-2} \cdot f \cdot t_{s1} \cdot i_{ox1})]}{(n_{3-2} \cdot f \cdot t_{s1}) - (n_{1-2} \cdot t_{s2})} \tag{Ic}$$

in which $f = t_{s3}/t_{s2}$ according to whether a current $i_{ox1}$ or $i_{ox2}$ respectively is applied in a first poststripping cycle, in which equations $n_{1-2}$ is the number of electrons transferred during the main stripping and $n_{3-2}$ is the number of electrons transferred during each of the two poststrippings;

and hence, the quantity of electroactive species present in the liquid sample is determined according to equation (II), namely:

$$[A] = t_{s1} \cdot (i_{ox1} + i_{chem}) \cdot V n_{1-2} F \quad \text{(II)}$$

in which equation (II) [A] is expressed in $\mu$mol/l, V is the sample volume in $\mu$l, and F is the faraday in coulombs per equivalents.

By virtue of the invention it is possible to reduce the electroanalysis time to a total duration not exceeding approximately five minutes.

The process according to the present invention is further characterized by at least any one of the following operating conditions:

the electrolysis according to stage (a) is performed during a period at least equal to 4 times t½, t½ being the half-reaction time of the electrolysis of the electroactive species; this period ensures a virtually complete reduction or oxidation of the electroactive species;

the main stripping current $i_{ox1}$ is between 0.1 $\mu$A and 500 $\mu$A and preferably between 20 and 40 $\mu$A;

the electrolysis according to the stage (a) lasts several minutes, whereas the post-electrolysis of the coulometric poststripping cycle lasts only a few seconds;

the current of another poststripping is approximately four times smaller than $i_{ox1}$;

the liquid sample analyzed additionally includes an agent modifying the electroactive and especially ionized species, promoting its electroanalysis;

the electroactive species is especially an ionized metal and the liquid sample containing it also includes a molar excess of oxidizing agents, such as mercury II and/or gold III;

the volume V of the liquid sample is at most equal to 100 $\mu$l and preferably between and 10 and 50 $\mu$l.

BRIEF DESCRIPTION OF THE DRAWINGS

FIGS. 1a and 1b show an electroanalysis device.

DESCRIPTION OF THE PREFERRED EMBODIMENTS

Figures 2A, 2B:
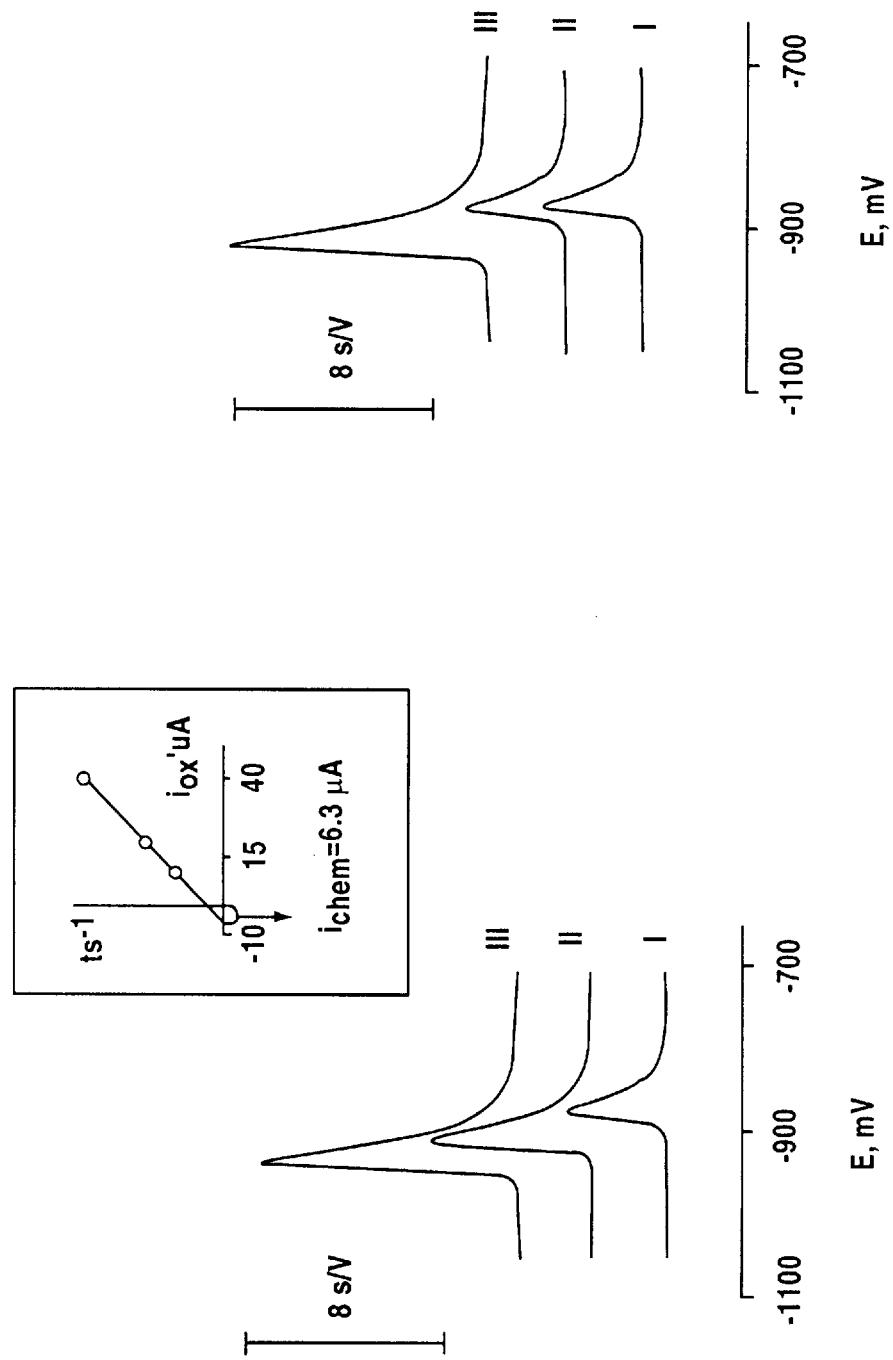
FIGS. 2a and 2b show stripping curves.
Figure 3:
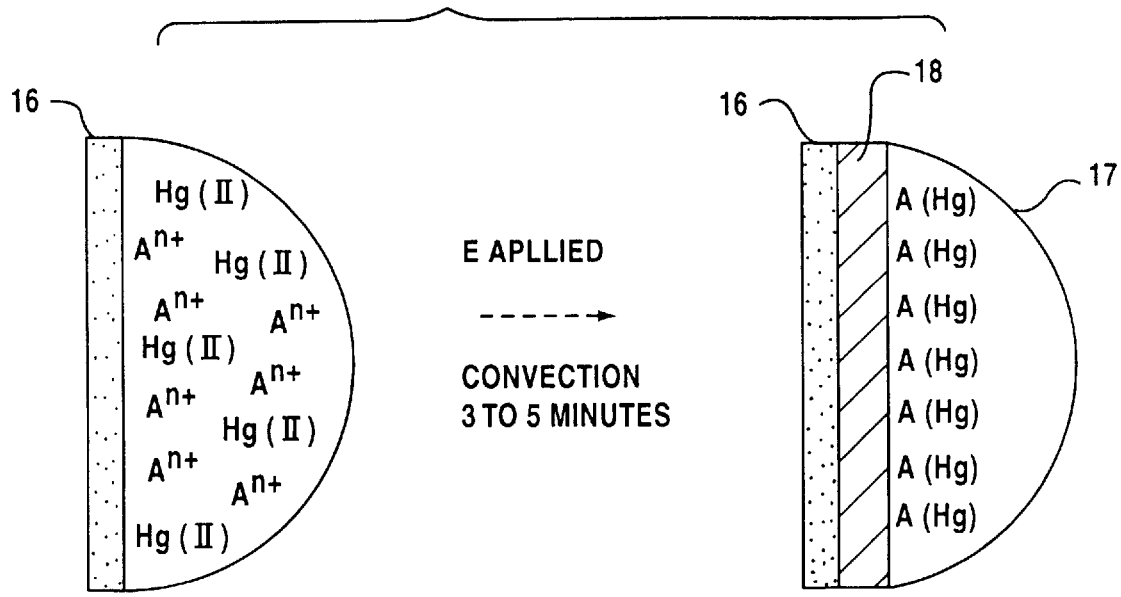
FIG. 3 shows formation of a mercury amalgam.
Figure 4:
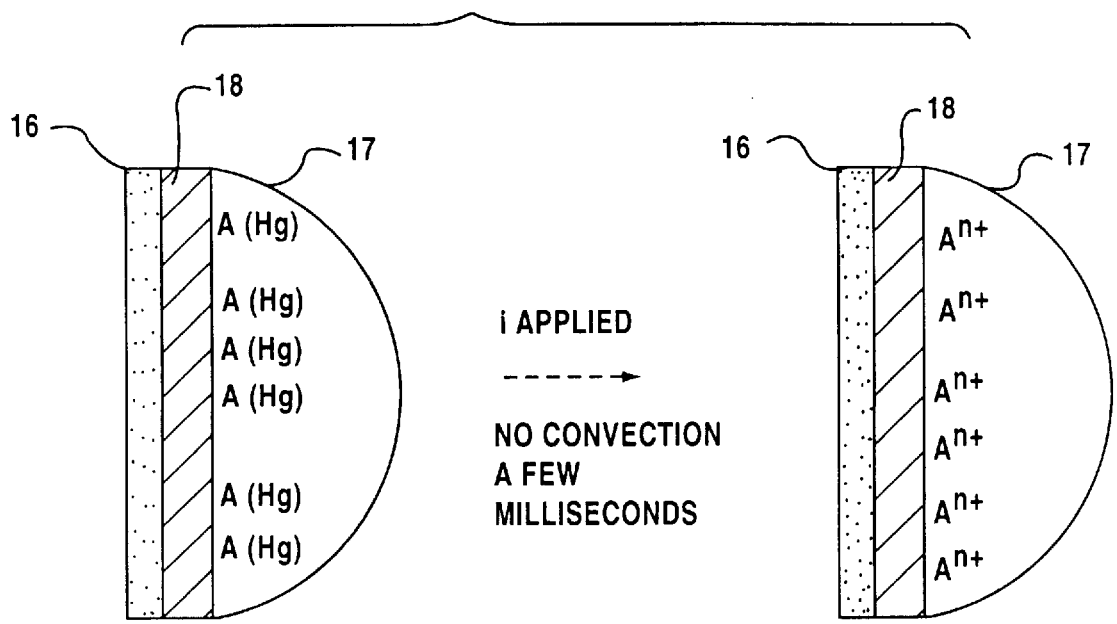
FIG. 4 shows a main coulometric stripping stage.
Figure 5:
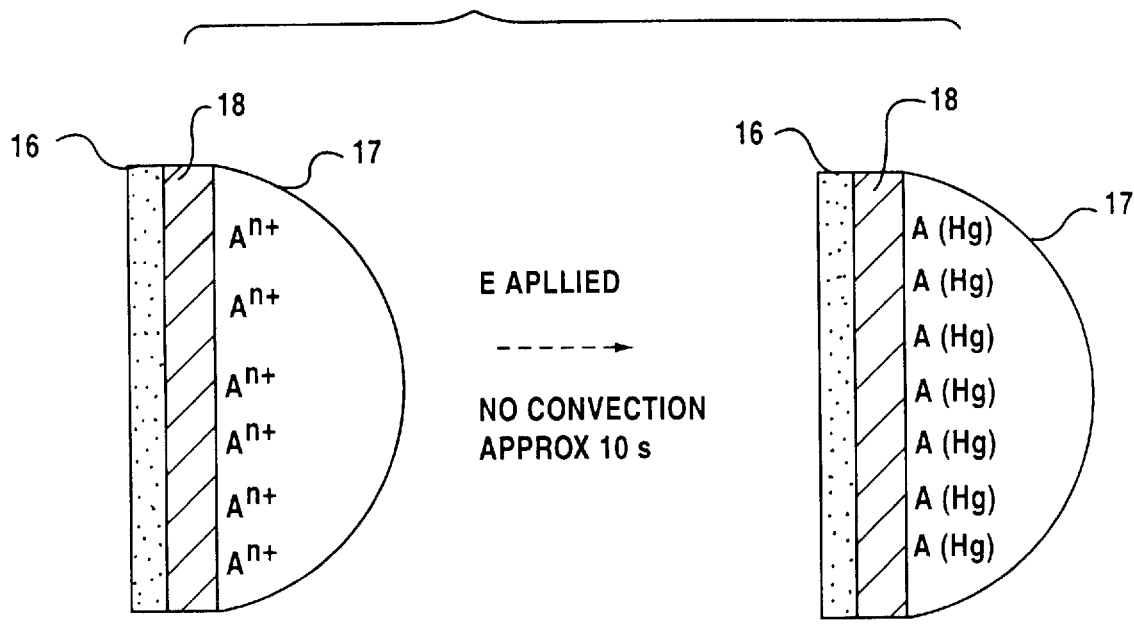
FIG. 5 shows a postelectrolysis step.
Figure 6:
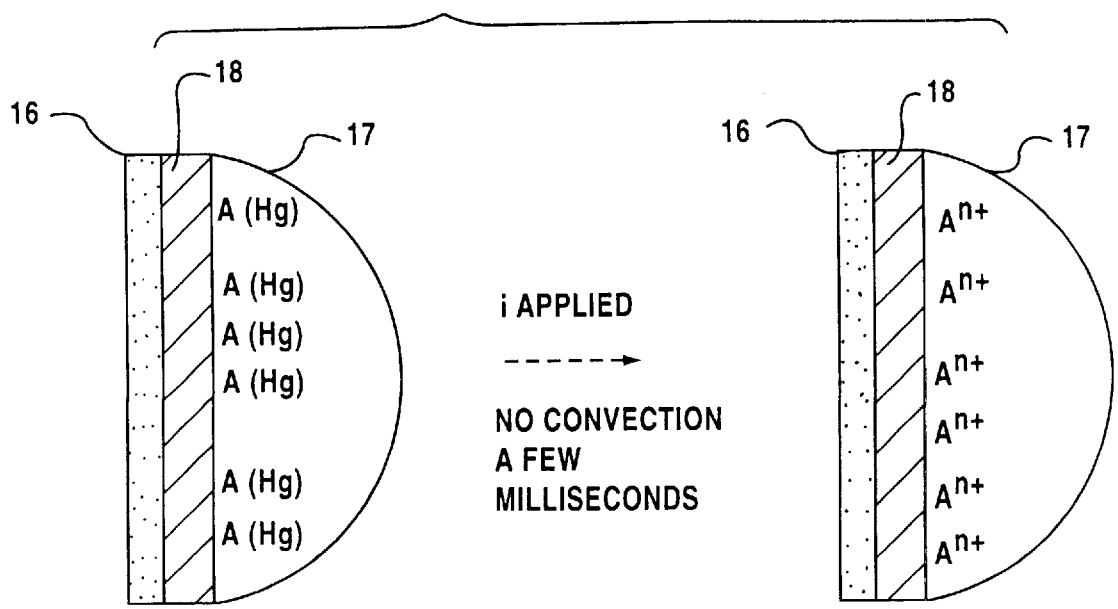
FIG. 6 shows a poststripping step.

FIG. 1 describes diagrammatically an electroanalysis device permitting especially the use of the particular process according to the invention, defined above. This device includes mainly an electrochemical cell 7 comprising, in a so-called "three-in-one" integrated manner, a reference electrode 8 of the Ag/AgCl type, a silver counterelectrode 9 and a working electrode 4 of the vitreous carbon type, with an electrically conductive liquid medium 6 ensuring an electrical connection or contact between the electrodes and the liquid sample 1 deposited, in the form of a drop, on the three electrodes.

The working electrode 4 itself includes two coaxial cylindrical glass enclosures, one external 7 and the other internal 15, a plug 4 forming the actual electrode, made of vitreous carbon, allowing a film of mercury to be supported, and in relation with an axial electrical conductor 5, and an annular plug 3 made of porous ceramic.

A removable ring 2 made of plastic enables the drop of liquid sample to be maintained on the front-facing and external surface of the working electrode 4.

A convection generator is associated with the electrochemical cell 7 and consists of a sleeve 10, adapted to receive the end of the cell 7 at the opposite end to the surface of contact with the liquid sample, and containing an electrical motor 11 the shaft of which is coupled to an eccentric 12.

The equipment described above is, for example, sold by the Applicant Company under reference TraceLab® 20.

This equipment comprises, inter alia, a unit 14, PSU22, for operating and controlling all the active components, including the electrodes, of the personal computer type, with an internal clock enabling measurements to be performed at a frequency at least equal to 0.1 kHz and preferably at least equal to 30 kHz. This operating and control unit is loaded with a program making it possible at the same time:

to control and steer the stages and steps of electroanalysis described above;

to regulate and control the operating parameters identified above;

to measure and store the output parameters and chiefly the coulometric stripping and coulometric poststripping times;

and to calculate the oxidation or reduction equivalent mean current, according to equation (I) and/or the quantity of electroactive, and especially ionized, species present, according to equation (II).

Such a program is, for example, loaded and marketed, but without the equations (I) and (II), by the Applicant Company under the name TAP2.

Various output peripherals can be used in combination with the operating and control unit, such as screen and printer.

The present invention is now described according to the following procedure, performed with the electroanalysis device described above, employing the following operating conditions:

the liquid for filling 6 the combined three-in-one electrode is 3M hydrochloric acid;

with the convection generator 11/12 the working cell, and hence the working electrode 4 are set in vibration during the electrolysis stage at a frequency of approximately 40 Hz, following an elliptical path the radii of which are 1 and 1.25 mm;

the volume of the liquid sample 1 placed on the working electrode is of the order of 10 to 50 $\mu$l before each analysis;

the spent mercury or gold film is wiped with a tissue impregnated with acidified ethanol, except in the case of the determination of copper II on gold film;

the electrolysis stage (a) is performed for a period at least equal to 4 times the electrolytic half-reaction time;

the vibratory convection regime generated by the motor 11 and the eccentric 12 is stopped during the final 10 seconds of the electrolysis before the main coulometric stripping stage (b) is entered;

the main coulometric stripping current, $i_{ox1}$, is between 20 and 40 $\mu$A; during this coulometric stripping stage the hydrodynamic regime, in vibration, is not taken up again;

each post-electrolysis step lasts approximately 10 seconds;

as already said, the poststripping current is equal to the main stripping current, insofar as the first poststripping cycle is concerned;

the second poststripping current is four times smaller than that in the main stripping, which is furthermore equal to the first poststripping current.

Determination of the Electrolytic Half-Reaction Time, Namely $t_{1/2}$

For each electroactive species this half-reaction time is determined by varying the electrolysis period. In the case of the various electroactive species investigated, this half-reaction time varies between 25 and 50 seconds. Consequently, a duration of the electrolysis stage (a) of the order of four minutes corresponds to at least four times the half-reaction time.

Determination of the Oxidation Equivalent Mean Current

By way of a check, the oxidation equivalent current is determined, on the one hand, according to the procedure of the invention as defined above, that is to say during the actual measurement and directly on the liquid sample being analyzed and, on the other hand, according to the prior art, that is to say using preliminary experiments separate from the actual analysis.

In this latter case each liquid sample is divided up into subsamples and each subsample is analyzed by employing different oxidation currents applied to the working electrode, $i_{ox}$. As already indicated, according to the prior art, the oxidation equivalent mean current, $i_{chem}$, is determined by a graphical representation of the reciprocal of the duration of the stripping stage, as a function of the current applied, and by extrapolation of the linear regression obtained for a zero oxidation current.

The two ways of determining the oxidation equivalent mean current are illustrated in FIG. 2, comprising two parts (a) and (b). FIG. 2a shows the stripping curves obtained after an electrolysis stage of four minutes at at least 1.25 volts, in three subsamples containing 0.2M hydrochloric acid, 600 mg/l of Hg(II) and 200 µg/l of Zn(II), and after a subsequent stripping with three currents equal to 40, 20 and 10 µA respectively (curves I to III in FIG. 2a).

The stripping curves in FIG. 2b were recorded by starting with a fourth subsample, while employing the same electrolysis potential. Curve I was obtained during the main stripping, with a current of 40 µA. Curve II was obtained during the first poststripping step, by employing a current also equal to 40 µA. Finally, curve III was obtained during the second poststripping step, while employing a current equal to 10 µA.

The oxidation equivalent mean current, $i_{chem}$, evaluated from FIG. 2a is equal to 6.3 µA and that obtained from FIG. 2b and from equation (I) is 6.2 µA. The agreement between these two values, remaining within the limit of the expected experimental errors, demonstrates the validity of the principles according to the invention.

Detection Limit

The detection limit in potentiometry with coulometric stripping depends on the real time of acquisition of the data by the operating and control unit. In order to detect and locate a stripping peak it is necessary for at least 20 to 30 measurements to have been made on this peak. With a measurement frequency of the order of 90 kHz, the time of appearance of a stripping peak may be at least 120 to 3030 µs. The detection limits indicated in Table I have been estimated from a temporal detection threshold of 0.30 ms.

Mercury-Soluble Elements

The elements which can be amalgamated, in most cases analyzed with a voltammetric or potentiometric stripping technique are Zn(II), Cd(II), Tl(I), Cu(II) and Bi(III). All these elements have been investigated according to the electroanalysis process of the invention, and the results are summarized in Table I below. In order to permit a comparison between these elements the same electrically conductive liquid was employed, namely 0.20M hydrochloric acid, in the presence of 600 mg/l of Hg(II). Also, the same electrolysis stage has been involved in the case of all these elements, according to a period of 4 minutes, including 10 seconds without the hydrodynamic regime specified above, and the same currents were applied to the working electrode, namely 40 µA during the main coulometric stripping stage and the first poststripping step, and 10 µA during the second poststripping step. The electrolysis potential for Cu(II) and Bi(III) was −0.70 V and −1.5 V in the case of the other elements. All the liquid samples had a volume of 12 µl, with three different concentrations, of 10, of 50 and of 200 µg/l respectively. The equivalent chemical currents detailed in Table I are those determined for a concentration of 200 µg/l.

As Table I shows, a good agreement exists between the concentrations introduced and the concentrations found according to the electroanalysis process of the invention. In the case of the values of 200 and 50 µg/l, the relative difference is actually less than 3% for the various elements. All the measurements performed retrieve the values of the concentrations introduced, with a ratio lower than 100%. In the case of five consecutive measurements of the same sample, all the results agree within 98%; the inaccuracy of 2% being predominantly attributed to errors linked with the pipetting of the 12-µl liquid samples.

As expected, the agreement between the concentrations introduced and the concentrations found is less good in the case of levels of the order of 10 µg/l. At these relatively low concentrations the stripping times are of the order of a few milliseconds, and this introduces some errors into the automated integration of the stripping peak. Where thallium is concerned it was shown that the stripping signal practically disappeared at a concentration of 10 µg/l. Separate experiments have shown, when lowering the Hg(II) concentration and the current applied to the working electrode, that the degrees of agreement between the values introduced and values found can be satisfactory below 10 µg/l. The potential for equilibrium between Tl(Hg) and Tl(I) is obviously less reversible than in the case of the other elements investigated, and this requires either a higher concentration of thallium in the mercury or slower oxidation kinetics, in order to determine the thallium concentration. The equivalent chemical currents detailed in Table I are between 6.4 µA in the case of zinc and 0.52 µA in the case of bismuth. The large difference between zinc and cadmium in terms of oxidation current is attributed to the contribution of the protons in the oxidation of amalgamated zinc in acidic solution. The chemical equivalent currents are much smaller in the case of copper and bismuth than in the case of cadmium and thallium, and this shows that the contribution of chemical oxidation starting with the dissolved oxygen is controlled kinetically and not by oxygen diffusion in the liquid sample.

The detection limits detailed in Table I show, as expected, that they are inversely proportional to the number of electrons involved in the oxidation of the element in question. As a result of the variations between the different chemical equivalent currents the relation between the detection limits of concentrations in Table I does not correspond exactly to a relation between integers. When these variations are corrected and when they are normalized with the detection limit threshold for Bi(III), the relations of the detection limits for Zn(II), Cd(II), Tl(I), Cu(II) and Bi(III) are 1.52, 1.51, 2.99, 2.98 and 1.00 respectively.

The electroanalysis process and device described above have the following overriding advantages:

they make it possible to detect and to analyse elements in trace form, which have a concentration of the order of a nanomole;

they provide high accuracy and repeatability;

a number of elements can be determined simultaneously, for example copper Cu(II) and lead Pb(II) in water, after addition of a modifying matrix, for example an acidified solution of Hg(II).

TABLE I

| Element | Conc. introduced µg/l | Conc. found | Stripping signal (duration) ms | Chemical current µA | Number of electrons | Detection limit | | |
|---|---|---|---|---|---|---|---|---|
| | | | | | | µg/l | nM | pg |
| Zn(II) | 200 | 196.1 | 149.7 | 6.4 | 2 | 0.40 | 6.1 | 4.8 |
| | 50 | 49.8 | 38.0 | | 2 | 0.39 | 6.0 | 4.7 |
| | 10 | 11.0 | 8.4 | | 2 | 0.36 | 5.5 | 4.3 |
| Cd(II) | 200 | 196.8 | 94.8 | 2.8 | 2 | 0.63 | 5.6 | 7.6 |
| | 50 | 51.4 | 24.7 | | 2 | 0.61 | 5.4 | 7.3 |
| | 10 | 10.5 | 5.0 | | 2 | 0.60 | 5.3 | 7.2 |
| Tl(I) | 200 | 199.4 | 26.1 | 3.2 | 1 | 2.30 | 11.2 | 27.6 |
| | 50 | 51.5 | 6.8 | | 1 | 2.21 | 10.8 | 26.5 |
| | 10 | 23.4 | 3.1 | | 1 | 2.41 | 11.8 | 28.9 |
| Cu(II) | 200 | 199.9 | 88.9 | 1.0 | 1 | 0.67 | 10.6 | 8.1 |
| | 50 | 49.8 | 22.1 | | 1 | 0.67 | 10.7 | 8.0 |
| | 10 | 8.8 | 3.9 | | 1 | 0.76 | 12.1 | 9.1 |
| Bi(III) | 200 | 198.7 | 81.5 | 0.52 | 3 | 0.74 | 3.5 | 8.9 |
| | 50 | 51.1 | 21.0 | | 3 | 0.71 | 3.4 | 8.6 |
| | 10 | 10.4 | 4.2 | | 3 | 0.71 | 3.4 | 8.6 |

According to another example the determination of nickel is possible by virtue of a complexing agent, for example a sodium dimethylglyoxime (DMG) salt. In accordance with stage (a) of the process according to the invention, this complexing is virtually exhaustive and the complex formed is adsorbed onto an electrode consisting of a film of mercury. The equation corresponding to this complexing and adsorption can be represented generally as follows:

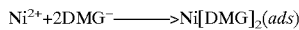

$$Ni^{2+} + 2DMG^- \longrightarrow Ni[DMG]_2(ads)$$

A reduction of the nickel is subsequently performed by cathodic stripping in accordance with stage (b) according to the present invention, and the following general equation:

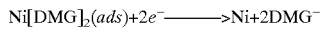

$$Ni[DMG]_2(ads) + 2e^- \longrightarrow Ni + 2DMG^-$$

In a specific example the quantity of nickel in a sample is determined by starting with a complex of 50 µg/l of nickel with DMG in a concentration equal to 0.1 mM in a pH6 phosphate buffer. The main cathodic stripping (step b) is performed at a current of 49 µA. The poststripping and calculation steps (c.b) are essentially the same in the case of the determination of heavy metals by amalgamation, the reoxidation of the nickel and readsorption of the complex being performed by an anodic electrolysis corresponding to step (c.a.). The determination of nickel by this technique has given the result of 49.7 µg/l of nickel present in the sample, compared with the known initial value of 50 µg/l.

We claim:

1. A process for the electroanalysis of at least one electroactive species, A, in an initial oxidation state (Eo), in trace form, in a liquid sample of volume V, by potentiometry with coulometric stripping, by employing a working electrode in electrical contact with said sample, said electroactive species being capable of being oxidized or reduced anew in solution, during the coulometric stripping, by an element dissolved in said sample, comprising the steps of:

(a) during a main stage performing one of an exhaustive electrolysis of the electroactive species, and an exhaustive complexing of said species with adsorption onto said electrode, while creating a convection regime in the vicinity of the liquid sample/working electrode interface, wherein practically all the electroactive species is deposited and retained, in a first oxidation state (EI), equal to or different from the initial state (EO), on the working electrode;

(b) during a main coulometric stripping stage, applying a predetermined current to the working electrode, causing a change in the oxidation state of the electroactive species (A), from the state (EI) to a state (EII), which is identical with or different from (Eo) in order to detach and diffuse practically all the electroactive species from said working electrode into the sample;

(c) performing at least twice the following coulometric poststripping cycle:

(c.a.) during a post-electrolysis step, applying a predetermined potential to the working electrode to change the oxidation state of the electroactive species (A) from the second state (EII) to a third state (EIII), which is identical with or different from (EI), of at least one portion of the electroactive species which has diffused into the liquid sample during the stripping stage (b);

(c.b.) during a poststripping step reapplying said predetermined current to the working electrode, causing a change in the oxidation state of the electroactive species (A) from the state (EIII) to the state (EII), in order to detach and diffuse said portion of the electroactive species from said working electrode into said liquid sample, wherein, by means of any one of the following operating conditions, namely:

(i) fixing the coulometric poststripping current during the previously defined step (c.b) of a poststripping cycle equal to the coulometric stripping current of the first stripping cycle (b), namely $i_{oxi}$, and fixing the coulometric poststripping current of another poststripping cycle, namely $i_{ox2}$, different from and smaller than $i_{oxi}$;

(ii) setting coulometric poststripping current, $i_{ox2}$, during the previously defined step (c.b) of a poststripping cycle different from, the main stripping current $i_{oxi}$, and setting the coulometric poststripping current $i_{ox2}$ of another poststripping cycle strictly equal to $i_{ox2}$;

measuring the main coulometric stripping time $t_{s1}$, and the coulometric times $t_{s2}$ and $t_{s3}$, of the at least two coulometric poststripping cycles respectively, and determining from the liquid sample alone, the oxidation or reduction equivalent mean current at the working electrode, $i_{chem}$, according to the equation (Ia), (Ib), for the first operating condition (i), or (Ic) for the second operating condition (ii):

$$i_{chem} = (t_{s3} \cdot i_{ox2} - f \cdot t_{s2} \cdot i_{ox1})/(f \cdot t_{s2} - t_{s3}) \tag{Ia}$$

in which f is equal to $(t_{s2}/t_{s1}) \cdot (n_{1-2}/n_{3-2})$ or $$i_{chem} = (\alpha i_{ox1} - i_{ox2})/(1-\alpha) \tag{Ib}$$

in which $\alpha = ((t_{s1} \cdot ts_3/t_{s2}^2) \cdot (n_{3-2}/n_{1-2}))^{1/2}$ or $$i_{chem} = \frac{((n_{1-2} \cdot t_{s2} \cdot i_{ox2}) - (n_{3-2} \cdot f \cdot t_{s1} \cdot i_{ox1}))}{(n_{3-2} \cdot f \cdot t_{s1}) - (n_{1-2} \cdot t_{s2})} \tag{Ic}$$

in which $f = t_{s3}/t_{s2}$ according to whether a current $i_{ox1}$ or $i_{ox2}$ respectively is applied in a first poststripping cycle, in which equation $n_{1-2}$ is the number of electrons transferred during the main stripping and $n_{3-2}$ is the number of electrons transferred during each of the two poststrippings, and determining the quantity of electroactive species (A) present in the liquid sample, according to equation (II):

$$(A) = t_{s1} \cdot (i_{ox1} + i_{chem}) \cdot V n_{1-2} F \tag{II}$$

in which equation (II), (A) is expressed in $\mu$mol/l, V is the sample volume in $\mu$l, and F is the faraday in coulombs per equivalents.

2. The process as claimed in claim 1, wherein the main stage is a stage of practically exhaustive electrolysis of the electroactive species.

3. The process as claimed in claim 1, wherein the main stage is a stage of exhaustive complexing of said species with adsorption onto said electrode.

4. The process as claimed in claim 1, wherein the electrolysis according to stage (a) is performed for a time at least equal to 4·t½, t½ being the half-reaction time of the electrolysis of the electroactive species (A).

5. The process as claimed in claim 1, wherein $i_{ox1}$ is between 0.1 $\mu$A and 500 $\mu$A.

6. The process as claimed in claim 1, wherein the electrolysis according to stage (a) lasts a predetermined number of minutes, whereas the post-electrolysis according to (c.a) lasts a predetermined number of seconds.

7. The process as claimed in claim 1, wherein $i_{ox2}$ is approximately four times smaller than $i_{ox1}$.

8. The process as claimed in claim 1, wherein the liquid sample additionally includes an agent for modifying the electroactive species.

9. The process as claimed in claim 1, in which the electroactive species is an ionized metal, wherein the liquid sample contains a molar excess of an oxidizing agent comprising mercury (II) or gold (III).

10. The process as claimed in claim 1, wherein the volume V of the liquid sample is at most 100 $\mu$l.

11. The process as claimed in claim 1, wherein the duration of the coulometric stripping stage does not exceed 1 s.

12. A process according to claim 1, wherein said main stage further includes the step of stopping the electrolysis and said convection regime.

13. A process according to claim 1, wherein during the poststripping step the operating condition (ii) includes setting the coulometric poststripping current during the previously defined step (c.b) of a poststripping cycle smaller than the main stripping current.

* * * * *